(12) United States Patent
Cheng et al.

(10) Patent No.: US 7,622,056 B2
(45) Date of Patent: Nov. 24, 2009

(54) HIGH DIELECTRIC ANISOTROPY LIQUID CRYSTAL COMPOUND AND COMPOSITION CONTAINING THE SAME

(75) Inventors: Kung-Lung Cheng, Hsinchu (TW);
Shih-Hsien Liu, Hsinchu County (TW);
Ann-Cheng Chen, Hsinchu (TW);
Peu-Jane Haung, Taipei (TW);
Chih-Lung Chin, Taoyuan County (TW)

(73) Assignees: Industrial Technology Research Institute, Hsinchu (TW); Daily Polymer Corporation, Kaohsiung Hsien (TW)

( * ) Notice: Subject to any disclaimer, the term of this patent is extended or adjusted under 35 U.S.C. 154(b) by 65 days.

(21) Appl. No.: 11/987,645

(22) Filed: Dec. 3, 2007

(65) Prior Publication Data
US 2008/0135803 A1 Jun. 12, 2008

(30) Foreign Application Priority Data
Dec. 6, 2006 (TW) ............................. 95145324 A

(51) Int. Cl.
*C09K 19/34* (2006.01)
*C09K 19/20* (2006.01)
*C09K 19/36* (2006.01)
*C07D 241/04* (2006.01)
*C07D 401/02* (2006.01)
*C07D 403/02* (2006.01)

(52) U.S. Cl. ............................. 252/299.61; 252/299.67; 252/299.7; 544/357; 544/358; 544/359; 544/360; 544/392; 544/395; 544/405

(58) Field of Classification Search ................. 428/1.1; 252/299.61, 299.67, 299; 544/298, 330, 544/336, 357, 358, 360, 392, 359, 395, 405
See application file for complete search history.

(56) References Cited
FOREIGN PATENT DOCUMENTS
JP 57206672 * 12/1982

* cited by examiner

*Primary Examiner*—Shean C Wu
(74) *Attorney, Agent, or Firm*—Birch, Stewart, Kolasch & Birch, LLP

(57) ABSTRACT

The invention relates to a high dielectric anisotropy liquid crystal compound which is a pyridyl derivative with substituents of electrons push-pull effect. Furthermore, the high dielectric anisotropy liquid crystal compounds are colorless and have high thermal and photo stability as well as high compatibility in a liquid crystal host. A liquid crystal composition containing the high dielectric anisotropy liquid crystal compound can reduce threshold voltage of cholesteric reflective displays, thus saving power and extending lifetime of driver ICs.

23 Claims, 3 Drawing Sheets

HIGH DIELECTRIC ANISOTROPY LIQUID CRYSTAL COMPOUND AND COMPOSITION CONTAINING THE SAME

FIELD OF THE INVENTION

The invention relates to a liquid crystal compound with high dielectric anisotropy, and more particularly to a liquid crystal composition containing the liquid crystal compound.

DESCRIPTION OF THE RELATED ART

Recently, in addition to high resolution of the display, a thinner and lighter product is also desired. A cholesteric liquid crystal is suitable for a portable liquid crystal display. The cholesteric liquid crystal has various advantages of high brightness, high contrast, wide view angle and no flashing. In addition, the cholesteric liquid crystal has a memory effect such that the display thereof can display a long time following shutdown of applied electric field. Thus, a cholesteric liquid crystal display has economical power consumption and average power consumption thereof is fiftieth of that of a transmissive liquid crystal display panel.

For the cholesteric liquid crystal display, it is important to reduce the threshold voltage. The key method of reducing the threshold voltage is the improvement of the liquid crystal material.

The threshold voltage (Vth) of the cholesteric liquid crystal relates to a dielectric anisotropy ($\Delta\in$), a coefficient of elasticity ($k_{ii}$), a helical pitch (p) of the formula as below:

$$Vth=\{k_{11}\pi^2+\theta^2[k_{33}-2k_{22}(1-\alpha)]\}^{1/2}/\in_0\Delta\in, \text{ wherein}$$
$$\alpha=2\pi d/p\theta$$

There are several ways to reduce the threshold voltage from the liquid crystal material for improvement as below:

1. The helical pitch of the liquid crystal material is increased.
2. A liquid crystal material with high dielectric anisotropy is used.
3. The coefficient of elasticity of the liquid crystal material is reduced.

From the above, changing the helical pitch of the cholesteric liquid crystal will affect the reflective wavelength expanding position thereof eliminating the suitability for the helical pitch to be adjusted. The coefficient of elasticity of the cholesteric liquid crystal is difficult to anticipate from the structure of the liquid crystal molecule. However, the dielectric anisotropy of the cholesteric liquid crystal can be anticipated from the structure and the substituent group of the liquid crystal molecule.

In addition to reducing the threshold voltage, ideal characteristics of a liquid crystal material include, for example, wide temperature range of liquid crystal phase (operative temperature is from −40 to 100° C.), good optical and chemical stability (life>20,000 hours), good compatibility between the liquid crystal molecules and the chiral dopants (solubility$\geqq$20%), contrast>10:1, and white light reflectivity>35%, etc.

Therefore, a liquid crystal material with high dielectric anisotropy for reducing the threshold voltage of the cholesteric liquid crystal display, while having wide liquid crystal phase, high stability and high compatibility is desired.

BRIEF SUMMARY OF THE INVENTION

The invention provides a liquid crystal compound of formula (I):

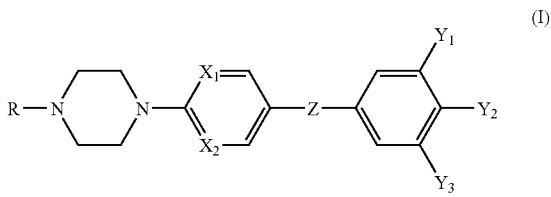

wherein each of $Y^1$, $Y^2$ and $Y^3$, independently, is selected from the group consisting of halogen, cyano or thiocyano group. Each of $X^1$ and $X^2$, independently, is selected from the group consisting of N or C. R is $C_{1-12}$ alkyl or $C_{1-12}$ alkoxyl. Z is ester or single bond.

The invention further provides a liquid crystal composition, comprising (a) 0.5 to 35% by weight of the liquid crystal compound of formula (I), and (b) 65 to 99.5% by weight of a liquid crystal host other than the liquid crystal compound of formula (I).

A detailed description is given in the following embodiments with reference to the accompanying drawings.

BRIEF DESCRIPTION OF THE DRAWINGS

The invention can be more fully understood by reading the subsequent detailed description and examples with reference to the accompanying drawings, wherein.

DETAILED DESCRIPTION OF THE INVENTION

Figure 1:
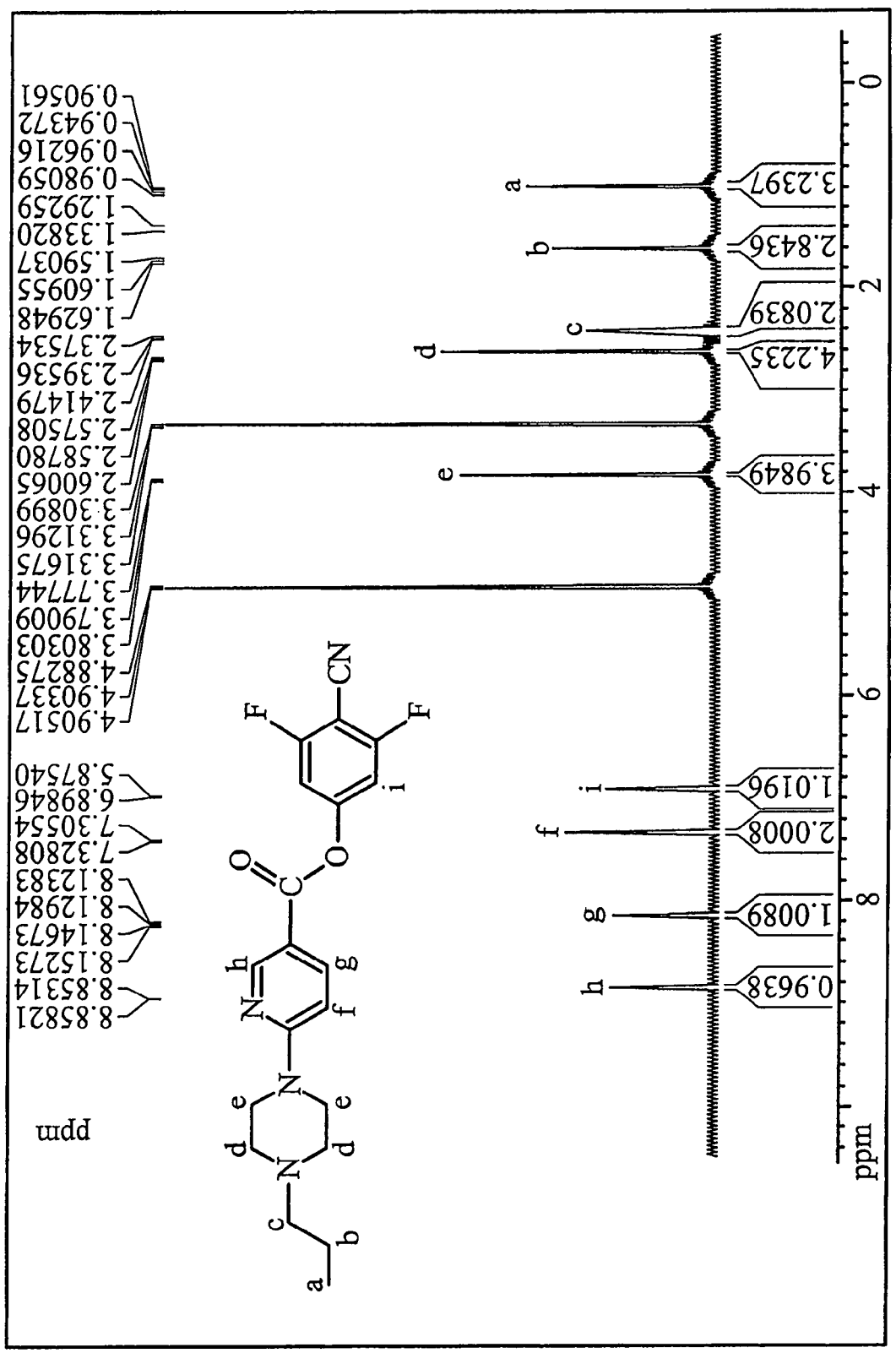
FIG. 1 shows a NMR spectrum of a liquid crystal compound I1 of Example 3.

The following description is of the best-contemplated mode of carrying out the invention. The description is provided for illustrating the general principles of the invention and is not meant to be limiting. The scope of the invention is best determined by reference to the appended claims.

The liquid crystal compound of formula (I) has a high dielectric anisotropy ($\Delta\in$) about 20-75.

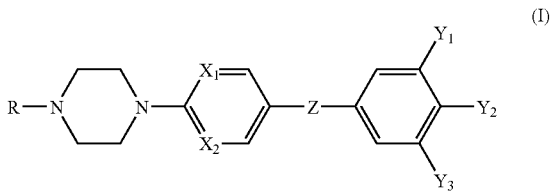

wherein each of $Y^1$, $Y^2$ and $Y^3$, independently, is selected from the group consisting of halogen, cyano or thiocyano group. Each of $X^1$ and $X^2$, independently, is selected from the group consisting of N or C. R is $C_{1-12}$ alkyl or $C_{1-12}$ alkoxyl. Z is ester or single bond.

In the compound of formula (I), $Y^1$, $Y^2$ and $Y^3$ are preferred F, CN and F respectively, $X^1$ and $X^2$ are preferred N and C respectively, and R is preferred $C_{3-6}$ alkyl.

In one embodiment of the invention, the liquid crystal compound with high dielectric anisotropy has a structure as below:

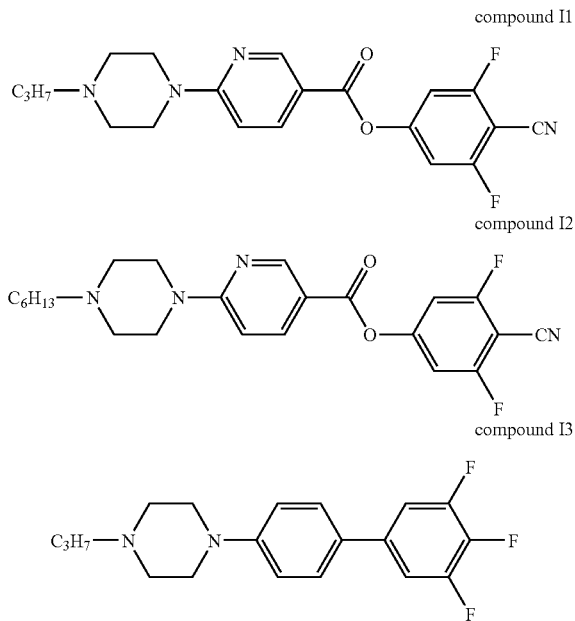

compound I1 compound I2 compound I3

The compound I1 has a dielectric anisotropy (Δ∈) about 70.5, compound I2 has a dielectric anisotropy (Δ∈) about 75.2, and compound I3 has a dielectric anisotropy (Δ∈) about 23, respectively.

The invention utilizes the chemical structure change of the liquid crystal compound to improve the chemical and physical photoelectric characteristics thereof for the application of a liquid crystal display element. In the chemical characteristics, an ideal liquid crystal material needs to have a wide nematic liquid crystal phase range, low melting point, low heat of fusion, chemical and physical stability and colorlessness. In the physical characteristics, the ideal liquid crystal material needs to have high dielectric anisotropy (Δ∈) and high birefringence (Δn).

The feature of the liquid crystal compound of the invention is the design of the molecule structure. The compound of formula (I) uses a functional group containing amino, R—N, to provide electrons for resonance, thus the dipole moment thereof is increased. In addition, the polar function groups of $Y^1$, $Y^2$ and $Y^3$ produce the electron push-pull effect such that the dielectric anisotropy of the liquid crystal molecule is enhanced.

Furthermore, if the liquid crystal compound with high dielectric anisotropy is colorful, only a trace of the liquid crystal compound is doped in a liquid crystal host to avoid interfering with display effect for producing color. However, the minor dopant is inefficient for reducing the threshold voltage of the display. Therefore, the liquid crystal compound of the invention chooses halogen, cyano or thiocyano group as the polar end groups, $Y^1$, $Y^2$ and $Y^3$, such that a high dielectric anisotropy liquid crystal compound with colorless, high dipole moment and low viscosity can be obtained. It is suitable for a twisted nematic liquid crystal display (TN-LCD) and a super twisted nematic liquid crystal display (STN-LCD) to reduce the threshold voltage thereof.

In addition, if a conjugate structure of the molecule main chain of the liquid crystal compound is elongated, the birefringence thereof can be increased. Thus, the high dielectric anisotropy liquid crystal compound of the invention has a benzene ring structure on the molecule main chain.

Now there is still no single liquid crystal compound which can satisfy the requested temperature range for a liquid crystal. But, if the melting point and the heat of fusion of various materials consisting of the liquid crystal mixture are lower, the melting point of the mixture is lower. The melting point of the liquid crystal compound of the invention is about 85 to 104° C., and the heat of fusion thereof is about 18.49 to 17.71 cal/g. Therefore, the liquid crystal compound of the invention can be used to make a liquid crystal eutectic mixture with low melting point for meeting the request of the temperature range of the liquid crystal phase.

In summary, the liquid crystal compound of the invention in addition to having high dielectric anisotropy, also has advantages of being colorless, highly thermal, photo stability and high compatibility in a liquid crystal host.

In the liquid crystal compound of formula (I), the compound IV having an ester group as Z can be prepared by the reactions below, taking $X^1$=N, and $X^2$=C as an example:

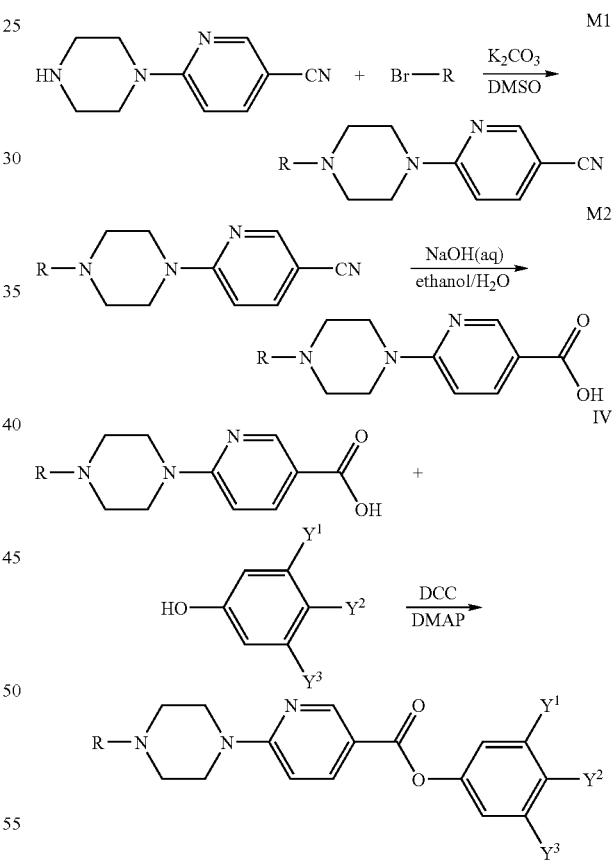

M1

M2

IV wherein R, $Y^1$, $Y^2$ and $Y^3$ are defined as above. One skilled in the art can readily appreciate that $X^1$ and $X^2$ can be replaced by other combinations, for example $X^1$ and $X^2$ can be both N or C.

In the above synthesis reactions, the intermediate products M1 and M2 and the high dielectric anisotropy liquid crystal compound IV are obtained by a reaction temperature of about 80 to 100° C. and a reaction time of about 16 hours. The yield rate of the compound M1, M2 and IV are about 30 to 90%.

In the liquid crystal compound of formula (I), the compound V having an single bond as Z can be prepared by the reactions below, taking $X^1$=N, and $X^2$=C as an example:

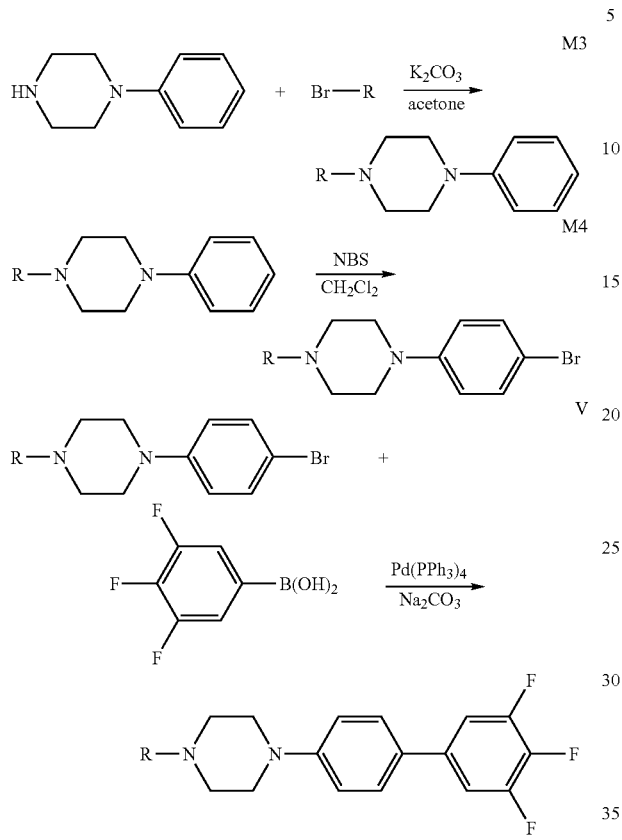

wherein R, $Y^1$, $Y^2$ and $Y^3$ are defined as above. One skilled in the art can readily appreciate that $X^1$ and $X^2$ can be replaced by other combinations, for example $X^1$ and $X^2$ can be both N or C.

In the above synthesis reactions, the intermediate products M3 and M4 and the high dielectric anisotropy liquid crystal compound V are obtained by a reaction temperature of about 80 to 100° C. and a reaction time of about 16 hours. The yield rate of the compound M3, M4 and V are about 30 to 90%.

The high dielectric anisotropy liquid crystal compound of the invention can effectively reduce the threshold voltage and has good compatibility with the liquid crystal. Further, it can be synthesized by simple steps and therefore provides an economic advantage.

In one aspect of the invention, a liquid crystal composition comprises:

(a) 0.5 to 35% by weight of the liquid crystal compound of formula (I), and (b) 65 to 99.5% by weight of a liquid crystal host other than the liquid crystal compound of formula (I).

In one embodiment of the invention, the liquid crystal compound of formula (I) is preferably 5 to 20% by weight of the liquid crystal composition. The liquid crystal host may be a liquid crystal host used in reflective cholesteric, polymer dispersed, twisted nematic (TN), super twisted nematic (STN), or in-plane switch (IPS) liquid crystal display.

The above liquid crystal host may comprise one or more compounds represented by formula (Z1) to formula (Z9) as below:

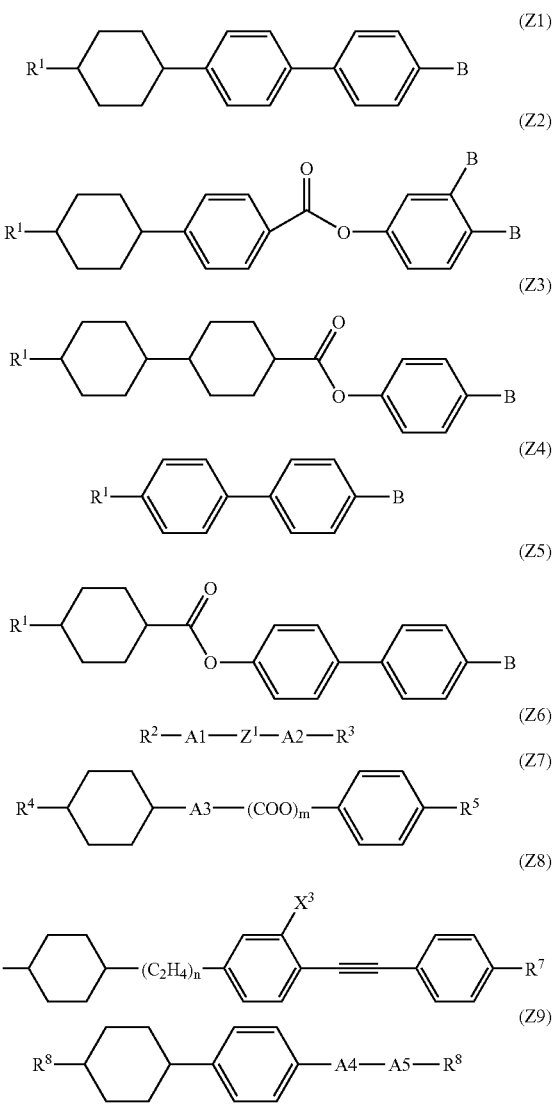

In the above formulas, each of $R^1$, independently, is $C_{1-9}$ alkyl. Each of B, independently, is halogen or cyano. Each of $R^2$, $R^3$, and $R^4$, independently, is $C_{1-10}$ alkyl in which one methylene group is optionally substituted by —O— or —CH=CH—, and one or more hydrogen atoms are optionally substituted by fluorine atom. Each of $R^5$ and $R^8$, independently, is $C_{1-10}$ alkyl in which one methylene group is optionally substituted by —O—. Each of $R^6$, $R^7$, and $R^9$, independently, is $C_{1-10}$ alkyl. Each of A1, A2, A3 and A5, independently, is trans-1,4-cyclohexylene or 1,4-phenylene. A4 is 1,4-phenylene in which one or more lateral hydrogen atoms are optionally substituted by fluorine atom. $Z^1$ is single bond or triple bond. Each of m and n, independently, is an integer of 0-2. $X^3$ is hydrogen or fluorine atom. In the above liquid crystal host compounds, the compound of formula (Z2) is preferred.

The synthesis steps and the related measurement results of the liquid crystal compounds I1, I2, and I3 are described in detail as below:

EXAMPLE 1

Synthesis of M1

The intermediate product M1, 6-(4-Propyl-piperazin-1-yl)-nicotinonitrile, was synthesized by the reaction below:

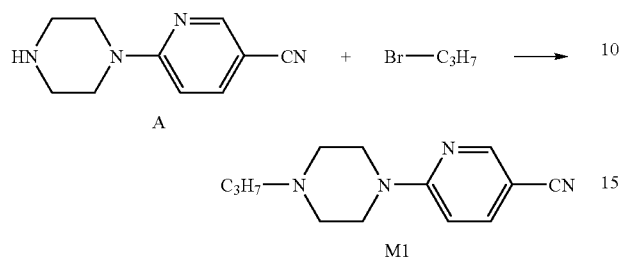

A compound A of 6-piperazin-1-yl-nicotinonitrile was performed an addition reaction of alkyl to obtain the intermediate product M1. In a nitrogen atmosphere, 1 g (5.3 mmol) of the compound A, 0.74 g (6 mmol) of n-propyl bromide, and 1.38 g (10 mmol) of potassium carbonate were placed in a reaction vase, and then a solvent of 20 ml of dimethyl sulfoxide (DMSO) was added. The mixture was heated to reflux at 100 to 110° C. for reaction for 16 hours, and then cooled to room temperature. After cooling, the resulting mixture was subjected to extraction with saturated salt water and ethyl acetate of several times until DMSO was removed completely, and then dried over anhydrous $MgSO_4$, filtered, and condensed. The residue was subjected to purification by column chromatography, and the intermediate product M1 as a yellow liquid was obtained in a 90% yield.

EXAMPLE 2

Synthesis of M2

The intermediate product M2, 6-(4-Propyl-piperazin-1-yl)-nicotinic acid, was synthesized by the reaction below:

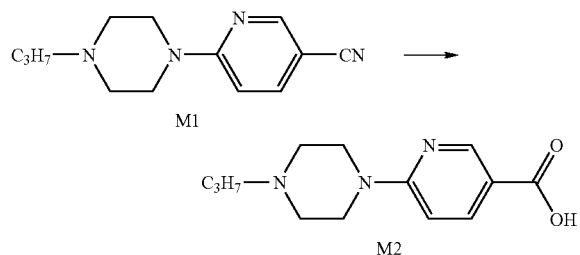

The intermediate product M1 synthesized from Example 1 was hydrolyzed to obtain the intermediate product M2. In the atmosphere, 1 g (4.3 mmol) of the intermediate product M1, and 0.4 g (10 mmol) of sodium hydroxide were placed in a reaction vase, and then a mixture liquid of 20 ml of ethanol and water with the ration 8:2 was added. The mixture was heated to reflux at 80° C. for reaction for 16 hours, and then cooled to room temperature. After cooling, the resulting mixture was dried and condensed to remove ethanol and water. The residue was subjected to an ice bath by using methanol to separate out sodium hydroxide, and then filtered, dried over anhydrous $MgSO_4$, and condensed to obtain the intermediate product M2 as a white solid in a 90% yield.

EXAMPLE 3

Synthesis of I1

The high dielectric anisotropy liquid crystal compound I1, 6-(4-Propyl-piperazin-1-yl)-nicotinic acid 4-cyano-3,5-difluoro-phenyl ester, was synthesized by the reaction below:

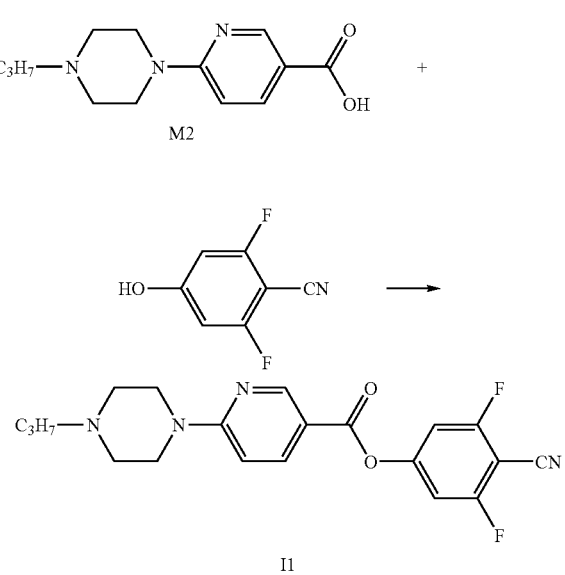

The intermediate product M2 was performed esterification to obtain the high dielectric anisotropy liquid crystal compound I1. In the atmosphere, 1 g (4.0 mmol) of the intermediate product M2, 0.7 g (4.5 mmol) of 2,6-Difluoro-4-hydroxy-benzonitrile, 1 g (5 mmol) of N,N-Dicyclo hexyl-carbodiimide (DCC), and 0.2 g of 4-Dimethylaminopyridine (DMAP) were placed in a reaction vase, and then 20 ml of acetonitrile was added. The mixture was heated to reflux at 80° C. for reaction for 16 hours, and then cooled to room temperature. After cooling, the resulting mixture was filtered, dried, and condensed to remove acetonitrile. Then, the resulting mixture was subjected to extraction with saturated salt water and ethyl acetate of two times, dried, and condensed. The residue was subjected to purification by column chromatography to obtain the liquid crystal compound I1 as a white solid in a 30% yield.

Then, the synthesis product I1 was measure by a NMR Spectrometer, and a NMR spectrogram thereof was shown as FIG. 1. The dielectric anisotropy of the synthesis product I1 was measured by a Liquid Crystal Analysis System 2 (LCAS-2), with the resulting dielectric anisotropy thereof 70.5.

Figure 2:
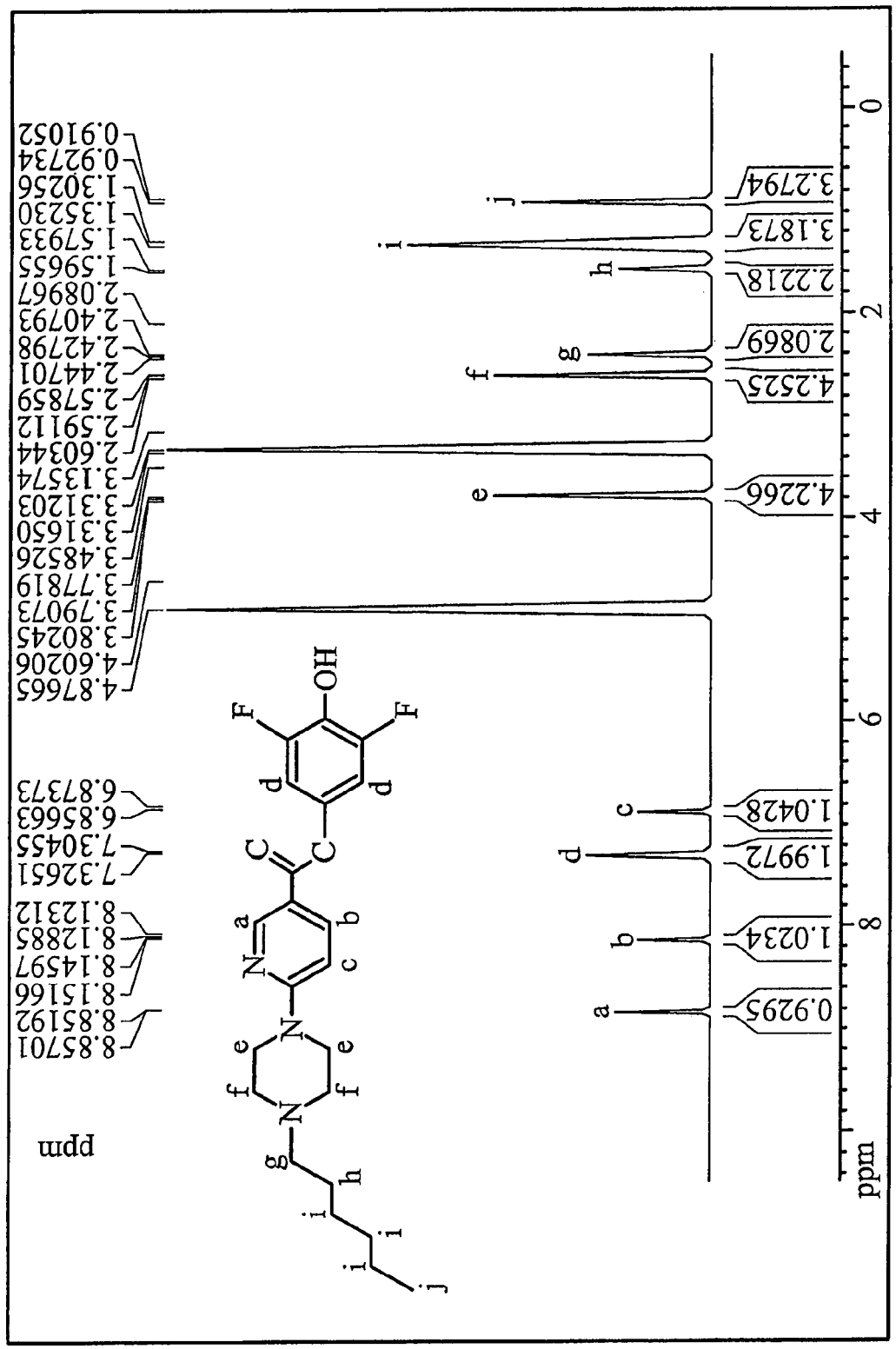
FIG. 2 shows a NMR spectrum of a liquid crystal compound I2 of Example 3.

The synthesis steps of the high dielectric anisotropy liquid crystal compound I2 of the invention were performed as above except for substituting the reactant of the addition reaction of alkyl with $BrC_6H_{13}$ in the synthesis of the intermediate product M1. The synthesis product I2 was measure by a NMR Spectrometer, and a NMR spectrum thereof was shown as FIG. 2. The dielectric anisotropy of the synthesis product I2 was measured by a Liquid Crystal Analysis System 2 (LCAS-2), and the resulting dielectric anisotropy thereof was 75.2.

EXAMPLE 4

Liquid Crystal Composition

A liquid crystal composition was provided by mixing 10% by weight of the high dielectric anisotropy liquid crystal compound I2 in Example 3 and 90% by weight of a liquid crystal mixture which is realized with the composition and properties given in the following table.

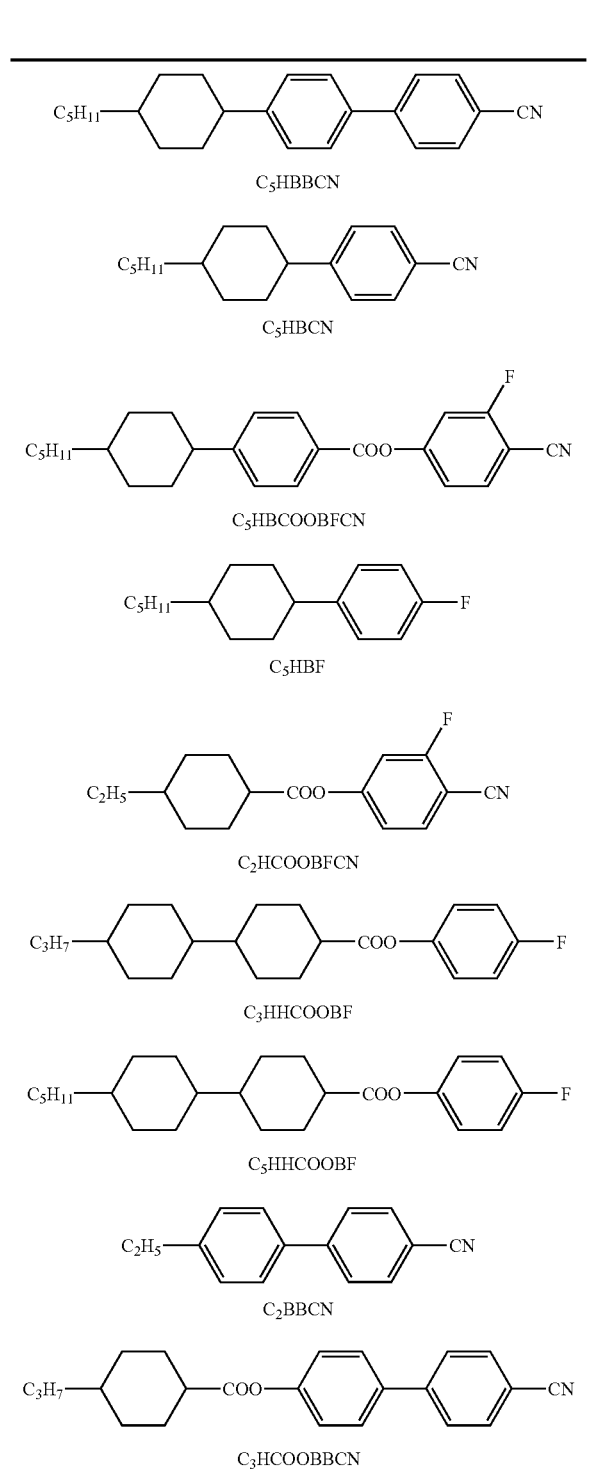

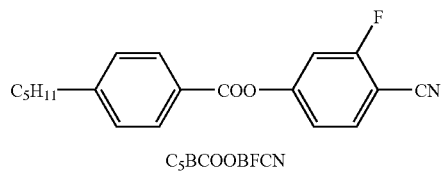

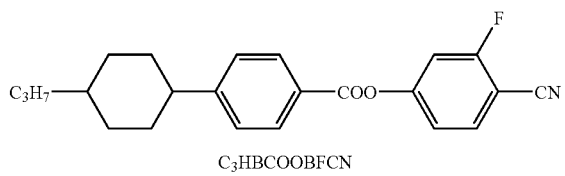

Liquid crystal mixture composition

| No. | Abbreviation | Conc./% |
|---|---|---|
| 1 | C₅HBBCN | 8 |
| 2 | C₅HBCN | 24.1 |
| 3 | C₅HBCOOBFCN | 7.7 |
| 4 | C₅HBF | 13.5 |
| 5 | C₂HCOOBFCN | 7 |
| 6 | C₃HHCOOBF | 6.5 |
| 7 | C₅HHCOOBF | 3.5 |
| 8 | C₂BBCN | 1.7 |
| 9 | C₃HCOOBBCN | 4.9 |
| 10 | C₅BCOOBFCN | 15.4 |
| 11 | C₃HBCOOBFCN | 7.7 |
|  |  | 100.0 |

The dielectric anisotropy of the liquid crystal mixture was 17.3, and the threshold voltage thereof was 1.09V. After mixing the high dielectric anisotropy liquid crystal compound I2 in Example 3 into the above liquid crystal mixture, the liquid crystal composition had a dielectric anisotropy of 23.21 and a threshold voltage of 0.76V.

EXAMPLE 5

Synthesis of M3

The intermediate product M3, 1-Phenyl-4-propyl-piperazine, was synthesized by the reaction below:

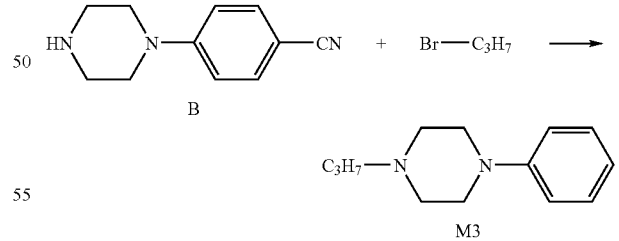

A compound B of 1-phenyl-piperazine was performed an addition reaction of alkyl to obtain the intermediate product M3. In a nitrogen atmosphere, 1 g (5.3 mmol) of the compound B, 0.74 g (6 mmol) of n-propyl bromide, and 1.38 g (10 mmol) of potassium carbonate were placed in a reaction vase, and then a solvent of 20 ml of acetone was added. The mixture was heated to reflux at 60 to 90° C. for reaction for 16 hours, and then cooled to room temperature. After cooling, the resulting mixture was subjected to extraction with saturated salt water and ethyl acetate of several times, dried by anhydrous MgSO$_4$, filtered, and condensed. The residue was subjected to purification by column chromatography, and the intermediate product M3 as a pale yellow liquid was obtained in a 90% yield.

EXAMPLE 6

Synthesis of M4

The intermediate product M4, 1-(4-bromo-phenyl)-4-propyl-piperazine was synthesized by the reaction below:

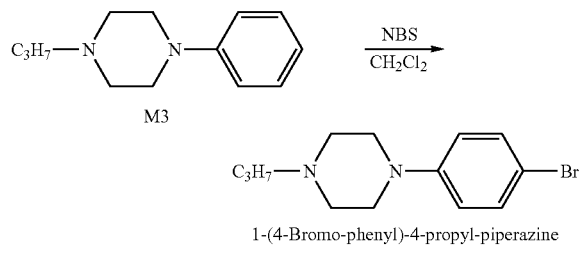

The intermediate product M3 synthesized from Example 5 was halogenated to obtain the intermediate product M4. In the atmosphere, 0.5 g (2.45 mmol) of the intermediate product M3 and 0.48 g (2.7 mmol) of N-bromosuccinimide (hereinafter NBS) were placed in a reaction vase, and then 20 ml of dichloromethane was added. The mixture was reacted for 16 hours at room temperature. The resulting mixture was subjected to extraction with saturated salt water and ethyl acetate of several times, dried by anhydrous MgSO$_4$, and condensed to obtain the intermediate product M4 as a white solid in a 70% yield.

EXAMPLE 7

Synthesis of I3

The high dielectric anisotropy liquid crystal compound I3, 1-propyl-4-(3,4,5-trifluorobiphenyl)-4-yl)piperazine, was synthesized by the reaction below:

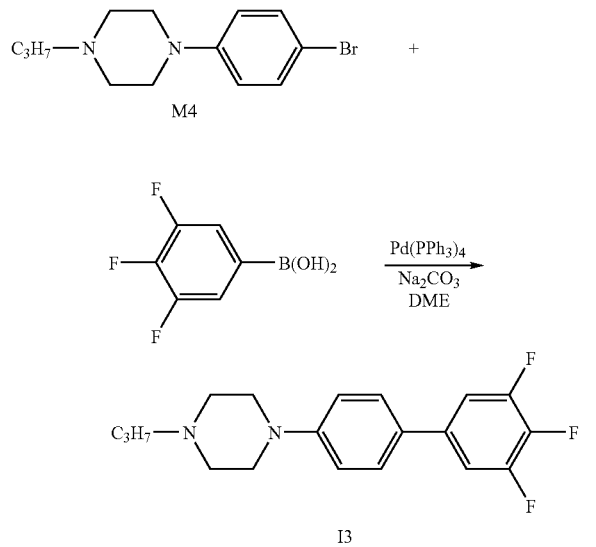

The intermediate product M4 was performed Suzuki coupling to obtain the high dielectric anisotropy liquid crystal compound I3. In the atmosphere, 0.6 g (2.1 mmol) of the intermediate product M4, 0.4 g (2.2 mmol) of 3,4,5-trifluorophenylboronic acid, 015 g (0.0001 mmol) of tetrakis(triphenylphosphine) palladium (0), and 2.34 g of sodium carbonate were placed in a reaction vase, and then 20 ml of 1,2-dimethyloxyethane (DME) and 13 ml of water were added. The mixture was heated to reflux at 80° C. for reaction for 16 hours, and then cooled to room temperature. After cooling, the resulting mixture was filtered through celite to remove black catalyst. Then, the resulting mixture was subjected to extraction with saturated salt water and ethyl acetate of two times, dried, and condensed. The residue was subjected to purification by column chromatography to obtain the liquid crystal compound I3 as a white solid in a 60% yield.

Figure 3:
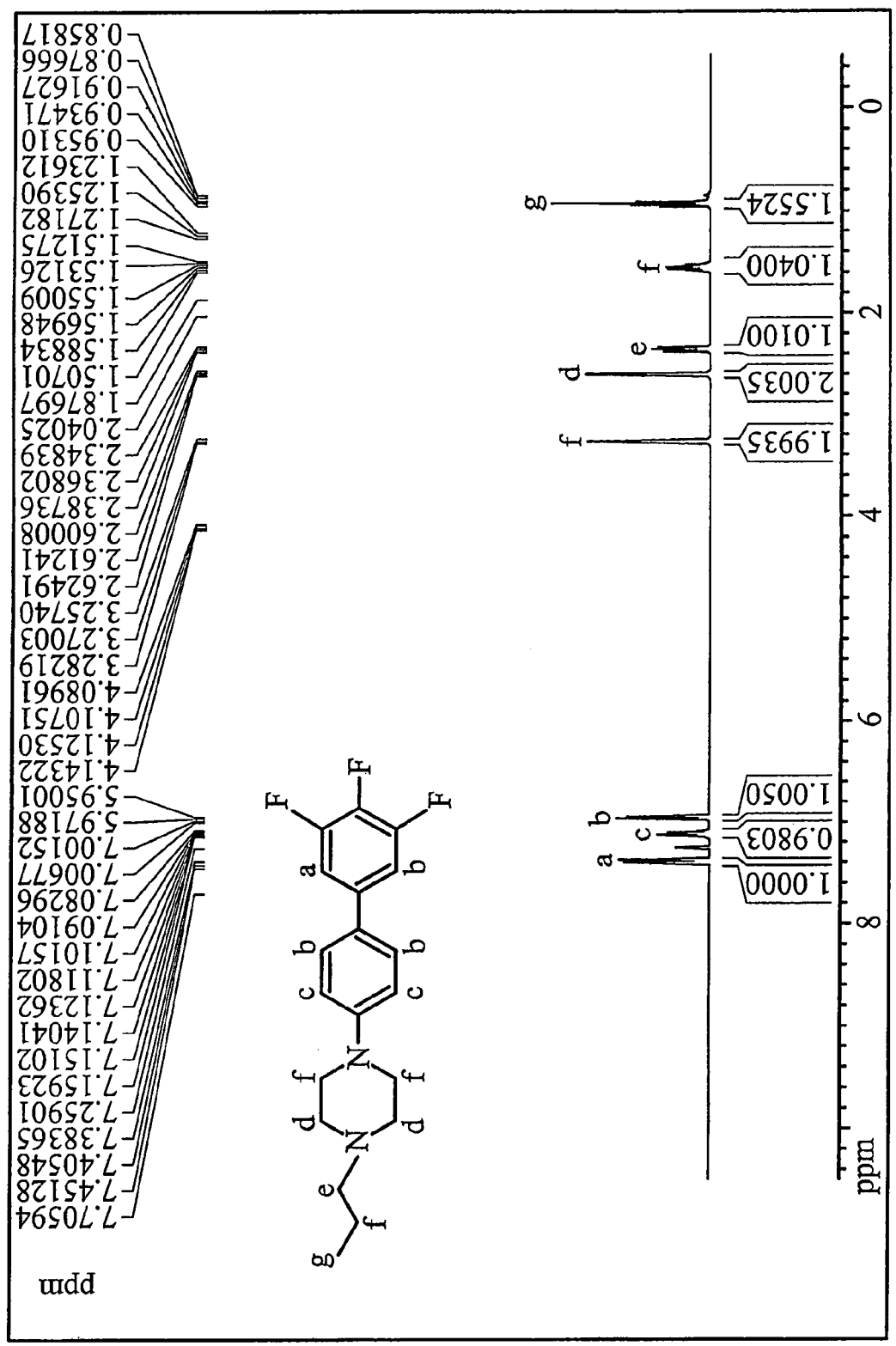
FIG. 3 shows a NMR spectrum of a liquid crystal compound I3 of Example 7.

Then, the synthesis product I3 was measure by a NMR Spectrometer, and a NMR spectrogram thereof was shown as FIG. 3. The dielectric anisotropy of the synthesis product I3 was measured by an LCAS-2, with the resulting dielectric anisotropy thereof 23.

EXAMPLE 8

Liquid Crystal Composition

A liquid crystal composition was provided by mixing 5% by weight of the high dielectric anisotropy liquid crystal compound I3 in Example 7 and 95% by weight of a liquid crystal mixture which is realized with the composition and properties given in the following table.

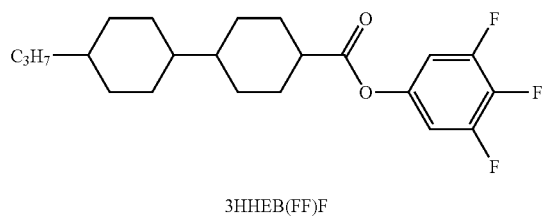

3HHEB(FF)F

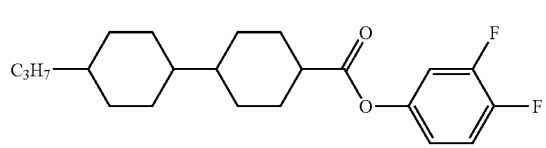

3HHEB(F)F

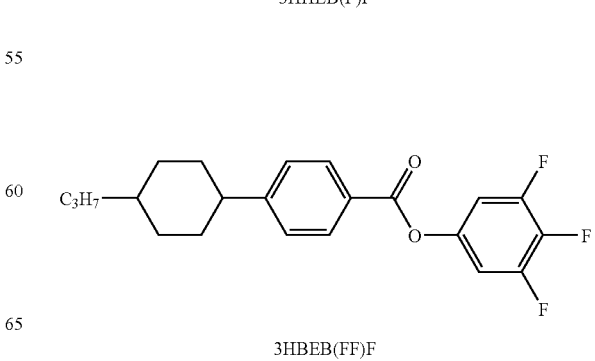

3HBEB(FF)F

-continued

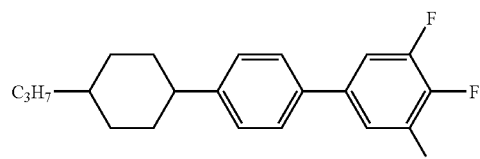

3HBB(FF)F

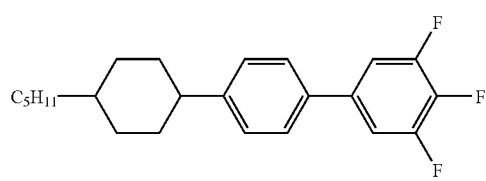

5HBB(FF)F

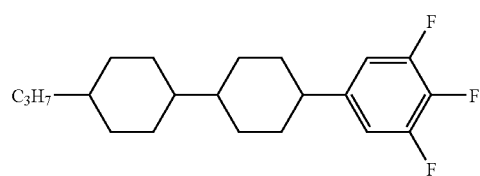

3HHB(FF)F

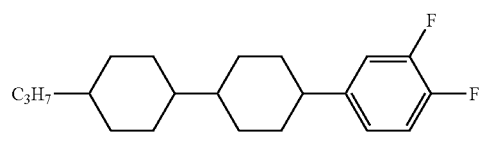

3HHB(F)F

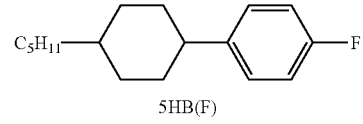

5HB(F)

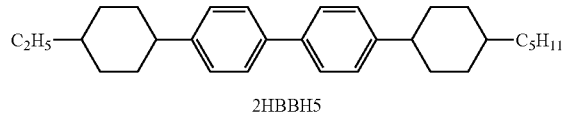

2HBBH5

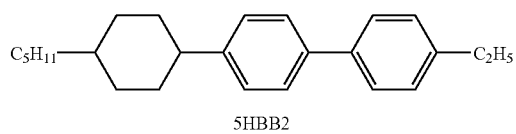

5HBB2

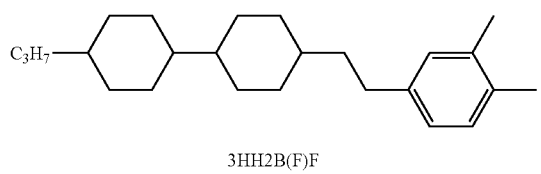

3HH2B(F)F

Liquid crystal mixture composition

| No. | Abbreviation | Conc./% |
|---|---|---|
| 1 | 3HHEB(FF)F | 8 |
| 2 | 3HHEB(F)F | 7 |
| 3 | 3HBEB(FF)F | 5 |
| 4 | 3HBB(FF)F | 10 |
| 5 | 5HBB(FF)F | 5 |
| 6 | 3HHB(FF)F | 5 |
| 7 | 3HHB(F)F | 7 |
| 8 | 5HBF | 8 |
| 9 | 2HB(F)BH5 | 5 |
| 10 | 2HB(F)BH5 | 5 |
| 11 | 5HBB2 | 5 |
| 12 | 3HH2B(F)F | 10 |

The dielectric anisotropy of the liquid crystal mixture was 7.33, and the threshold voltage thereof was 1.85V. After mixing the high dielectric anisotropy liquid crystal compound I3 in Example 7 into the above liquid crystal mixture, the liquid crystal composition had a dielectric anisotropy of 8.07 and a threshold voltage of 1.79V.

As a result, mixing the high dielectric anisotropy liquid crystal compound of the invention into the liquid crystal host can enhance the dielectric anisotropy of the liquid crystal composition and reduce the threshold voltage thereof, thus enhancing the performance of the liquid crystal display.

COMPARATIVE EXAMPLES 1~3

Liquid Crystal Compositions

A liquid crystal composition of Comparative Example 1 was provided by mixing 2% by weight of a liquid crystal compound A as shown below into a liquid crystal host containing cyanophenyl group.

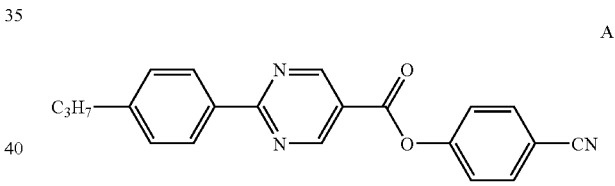

A

The threshold voltage measurement of the liquid crystal composition of Comparative Example 1 was shown in Table 1.

A liquid crystal composition of Comparative Example 2 was provided by mixing 15% by weight of a liquid crystal compound B as shown below into a liquid crystal host containing cyanophenyl group.

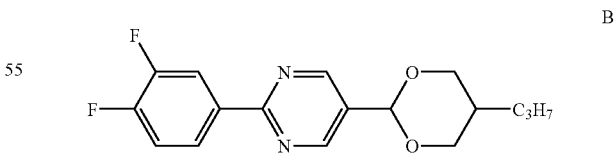

B

The threshold voltage measurement of the liquid crystal composition of Comparative Example 2 was shown in Table 1.

A liquid crystal composition of Comparative Example 3 was provided by mixing 2% by weight of a liquid crystal compound C as shown below into a liquid crystal host containing cyanophenyl and ester groups.

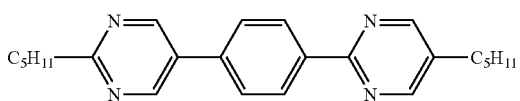

The threshold voltage measurement of the liquid crystal composition of Comparative Example 3 was shown in Table 1.

The result of threshold voltage measurement for liquid crystal compositions as described in Example 4 and Comparative Examples 1 to 3 are shown in Table 1.

TABLE 1

Threshold voltage change of liquid crystal compositions as described in Example 4 and Comparative Examples 1 to 3

| | The dielectric anisotropy ($\Delta\epsilon$) of liquid crystal compound | The threshold voltage (Vth) of liquid crystal host | The threshold voltage (Vth) of liquid crystal composition | The decrease of threshold voltage (%) |
|---|---|---|---|---|
| Comparative Example 1 | 31.2 | 1.54 | 1.46 | 5.2 |
| Comparative Example 2 | 28.5 | 1.54 | 1.46 | 5.2 |
| Comparative Example 3 | 21.2 | 1.54 | 1.54 | 0 |
| Example 4 | 75.2 | 1.09 | 0.76 | 30 |

As shown in Table 1, the liquid crystal composition of Example 4 containing high dielectric anisotropy liquid crystal compound of the invention can reduce the threshold voltage about 30% more than Comparative Examples 1 to 3. The liquid crystal compounds mixed into the compositions of Comparative Examples 1 to 3 are nitrogen-containing heterocyclic derivatives, and the maximum dielectric anisotropy thereof is 31.2. Thus, the maximum decrease of threshold voltage of the liquid crystal compositions can only achieve about 5.2%.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A liquid crystal compound of formula (I):

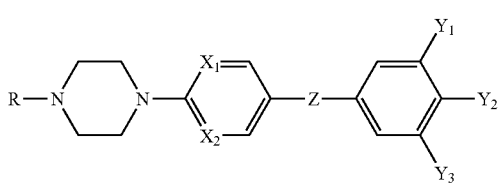

(I)

wherein each of $Y^1$, $Y^2$ and $Y^3$, independently, is selected from the group consisting of halogen, cyano or thiocyano group;

each of $X^1$ and $X^2$, independently, is selected from the group consisting of N or C;

R is $C_{1-12}$ alkyl or $C_{1-12}$ alkoxyl; and

Z is ester or single bond.

2. The liquid crystal compound as claimed in claim 1, wherein $Y^1$ is F, $Y^2$ is cyano, $Y^3$ is F, and Z is ester.

3. The liquid crystal compound as claimed in claim 1, wherein $Y^1$ is F, $Y^2$ is F, $Y^3$ is F, and Z is single bond.

4. The liquid crystal compound as claimed in claim 1, wherein $X^1$ is N and $X^2$ is C.

5. The liquid crystal compound as claimed in claim 1, wherein $X^1$ is C and $X^2$ is C.

6. The liquid crystal compound as claimed in claim 1, wherein R is $C_{3-6}$ alkyl.

7. The liquid crystal compound as claimed in claim 1, which is

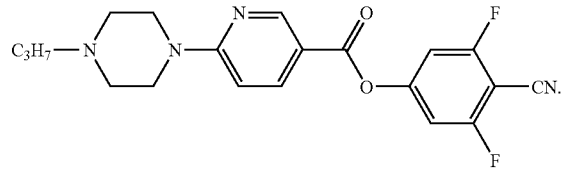

8. The liquid crystal compound as claimed in claim 1, which is

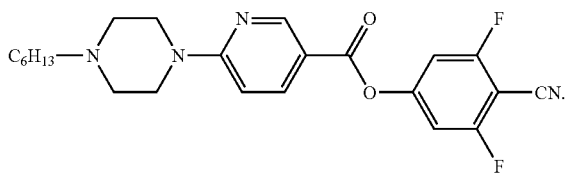

9. The liquid crystal compound as claimed in claim 1, which is

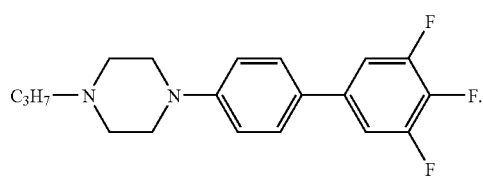

10. The liquid crystal compound as claimed in claim 1, having a dielectric anisotropy ($\Delta\epsilon$) of 20 to 75.

11. The liquid crystal compound as claimed in claim 1, which is a colorless liquid crystal compound.

12. A liquid crystal composition, comprising:
(a) 0.5 to 35% by weight of the liquid crystal compound as claimed in claim 1; and
(b) 65 to 99.5% by weight of a liquid crystal host other than the liquid crystal compound as claimed in claim 1.

13. The liquid crystal composition as claimed in claim 12, wherein the liquid crystal host is used in a liquid crystal display.

14. The liquid crystal composition as claimed in claim 13, wherein the liquid crystal display is reflective cholesteric, polymer dispersed, twisted nematic, super twisted nematic, or in-plane switch (IPS) liquid crystal display.

15. The liquid crystal composition as claimed in claim 10, wherein the liquid crystal host comprises one or more compounds represented by formula (Z1) to formula (Z9),

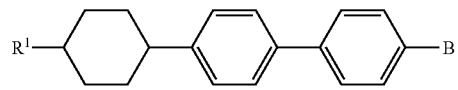
(Z1)

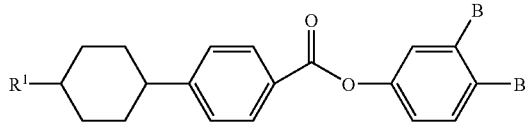
(Z2)

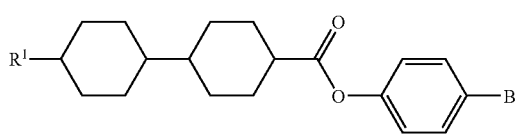
(Z3)

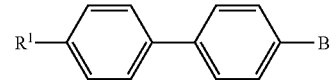
(Z4)

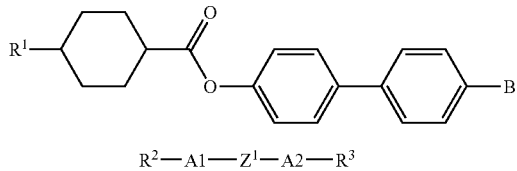
(Z5)

R²—A1—Z¹—A2—R³ (Z6)

R⁴—⬡—A3—(COO)ₘ—⬢—R⁵ (Z7)

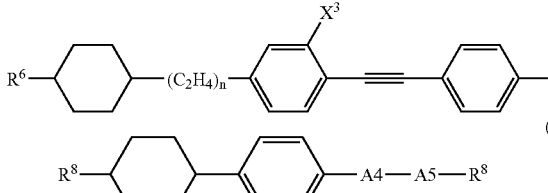
(Z8)

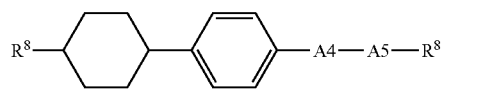
(Z9)

wherein each of R¹, independently, is $C_{1-9}$ alkyl;
each of B, independently, is halogen or cyano;
each of R², R³, and R⁴, independently, is $C_{1-10}$ alkyl in which one methylene group is optionally substituted by —O— or —CH=CH—, and one or more hydrogen atoms are optionally substituted by fluorine atom;
each of R⁵ and R⁸, independently, is $C_{1-10}$ alkyl in which one methylene group is optionally substituted by —O—;
each of R⁶, R⁷, and R⁹, independently, is $C_{1-10}$ alkyl;

each of A1, A2, A3 and A5, independently, is trans-1,4-cyclohexylene or 1,4-phenylene;
A4 is 1,4-phenylene in which one or more lateral hydrogen atoms are optionally substituted by fluorine atom;
Z¹ is single bond or triple bond;
each of m and n, independently, is an integer of 0-2; and
X³ is hydrogen or fluorine atom.

16. The liquid crystal composition as claimed in claim 12, wherein the liquid crystal compound is

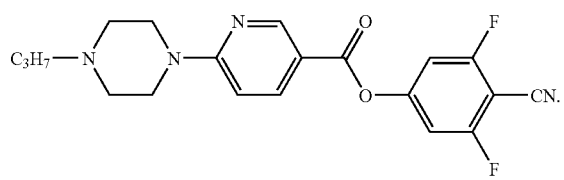

17. The liquid crystal composition as claimed in claim 12, wherein the liquid crystal compound is

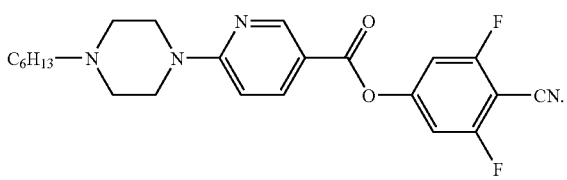

18. The liquid crystal composition as claimed in claim 12, wherein the liquid crystal compound is

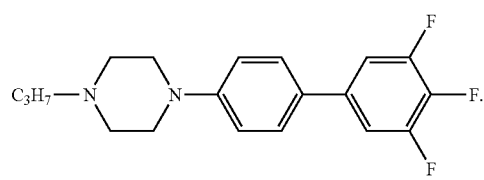

19. The liquid crystal composition as claimed in claim 16, wherein the liquid crystal compound constitutes 5 to 20% by weight of the liquid crystal composition.

20. The liquid crystal composition as claimed in claim 17, wherein the liquid crystal compound constitutes 5 to 20% by weight of the liquid crystal composition.

21. The liquid crystal composition as claimed in claim 18, wherein the liquid crystal compound constitutes 5 to 20% by weight of the liquid crystal composition.

22. The liquid crystal composition as claimed in claim 12, wherein the liquid crystal compound has a dielectric anisotropy (Δε) of 20 to 75.

23. The liquid crystal composition as claimed in claim 12, wherein the liquid crystal compound is colorless.

* * * * *